United States Patent [19]

Weissman

[11] 4,205,444
[45] Jun. 3, 1980

[54] DENTAL TOOL SHANK
[75] Inventor: Bernard Weissman, New York, N.Y.
[73] Assignee: IPCO Hospital Supply Corporation, White Plains, N.Y.
[21] Appl. No.: 928,557
[22] Filed: Jul. 27, 1978
[51] Int. Cl.² .................................................. A61C 1/10
[52] U.S. Cl. ...................................... 433/165; 433/128
[58] Field of Search .................... 32/48, 15, 7, 6, 27, 32/26

[56] References Cited
U.S. PATENT DOCUMENTS

| | | | |
|---|---|---|---|
| 418,108 | 12/1889 | Brown | 32/48 |
| 3,343,443 | 9/1967 | Moore | 32/15 |
| 4,053,982 | 10/1977 | Weissman | 32/15 |

*Primary Examiner*—Robert Peshock
*Attorney, Agent, or Firm*—Friedman, Goodman & Teitelbaum

[57] ABSTRACT

A dental tool such as a drill, burr, anchor and the like which is receivable in a dental hand piece for operative positioning thereof with respect to the teeth of a patient, the dental tool having a body member provided with an operative end portion for association with the teeth and a shank extending from the operative end portion for association with the hand piece. The head portion of the shank is provided with a first arrangement including a flat surface to provide driving engagement between the shank and the hand piece, and a circumferential groove for receiving a latching member of the hand piece for removably engaging the shank in the hand piece. A second similar arrangement is spaced downwardly on the head portion, where additional arrangements may be provided on the shank downwardly along the head portion as desired to provide a series of locations for driving and latching the shank in the hand piece. Preferably, a circumferential notch is provided in the shank between each of the arrangements to permit the severance of the uppermost arrangement or arrangements from the shank to reduce the length of the shank for insertion into the dental hand piece to permit convenient access to operative areas of the patient's mouth.

18 Claims, 8 Drawing Figures

DENTAL TOOL SHANK

BACKGROUND OF THE INVENTION

The present invention relates to dentistry in general, and more particularly to a dental tool shank which permits a variable longitudinal extension of the shank from a hand piece associated therewith for convenient access to operative areas of the patient's mouth, where preferably an upper head portion of the shank may be severed from the body of the shank to reduce the length of the shank.

In the use of dental hand pieces in the mouth of a patient, it is often found that the jaw-separation of the patient is inadequate to allow the head of the hand piece carrying a suitable attachment such as a drill, burr, anchor and the like to be placed in operative position with respect to the teeth of the patient, especially the posteriors. In the vestibular area of the mouth, it has also been found that the cheek and the tongue do not readily permit access to the normal hand piece provided with conventional tooth attachment extensions.

It is noted, that a prior art adjustable rotatable tool and a holder therefor is disclosed in my U.S. Pat. No. 3,576,076, showing a drill having a straight shank provided with graduated recesses along its length for selectively positioning the drill within the holder. The holder is provided with a spring locking member for releasably holding the drill at the selected position. The head portion of the holder is provided with a flat surface and a circumferential groove for mounting within a dental hand piece.

SUMMARY OF THE INVENTION

Accordingly, it is an object of the present invention to provide a drill, burr, anchor and the like with a shank which overcomes the disadvantages of the prior art.

Another object of the present invention is to provide a shank as set forth above wherein the extension of the dental tool can be varied to permit convenient access to the operative areas of the patient without discomfort.

A further object of the present invention is to provide a shank as set forth above which can be shortened by the dentist so as to limit the extension of the tool.

Still another object of the present invention is to provide a shank as set forth above which includes at least two driving and latching arrangements at the head portion thereof, where either arrangement can be utilized with a hand piece.

Yet another object of the present invention is to provide a shank as set forth above which includes a circumferential notch disposed between each driving and latching arrangement to permit the severance of the uppermost arrangement from the body member of the shank.

An added object of the present invention is to provide a dental tool shank as set forth above which can be readily inserted into a sleeve of a conventional hand piece, being located so that the selected driving and latching arrangement is achieved at any one of the designated locations to obtain the desired longitudinal extension of the shank from the hand piece for permitting convenient access to the operative areas of the patient's mouth.

These objects are achieved in accordance with the present invention, wherein the dental tool includes a body member provided with an operative end portion for association with the teeth of a patient and a shank extending from the operative end portion for association with a conventional dental hand piece, the shank being provided with first means for removably engaging the shank in the hand piece, and second means for providing driving engagement between the shank and the hand piece. The first engaging means include at least two longitudinally spaced apart circumferential grooves in the shank for selectively receiving a latching member of the hand piece in one of the grooves to vary the longitudinal extension of the shank from the hand piece, and the second driving means including a longitudinally extending flat surface on the shank for driving engagement with the hand piece, with first and second portions of the flat surface cooperating with the two grooves respectfully in each selected extension of the shank. The shank further includes third notch means to facilitate severance of an end portion of the shank for shortening the longitudinal extension of the shank to permit convenient access to the operative areas of the patient's mouth. The shank includes at least portions of the first engaging means and the second driving means in each selected length thereof so that at least one portion of the flat surface and at least one groove always remains on the shank, the third notch means being disposed between the longitudinally spaced apart grooves.

BRIEF DESCRIPTION OF THE DRAWINGS

With the above and additional objects and advantages in view, as will hereinafter appear, this invention comprises the devices, combinations and arrangements of parts hereinafter described by way of example and illustrated in the accompanying drawings of a preferred embodiment in which.

DETAILED DESCRIPTION OF THE PREFERRED EMBODIMENT

Figure 1:
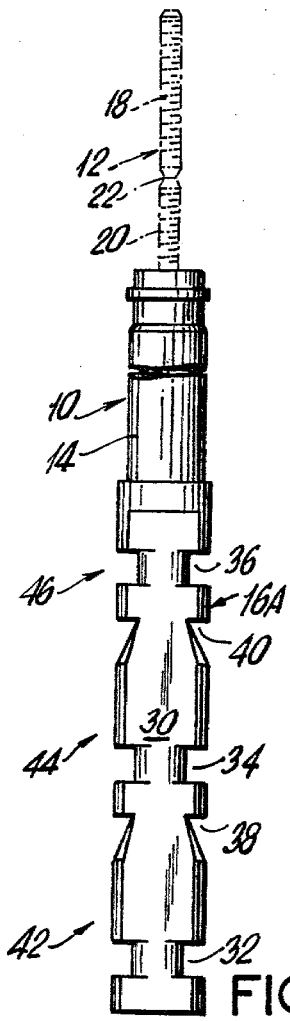
FIG. 1 is an elevational view of a dental tool such as a dental anchor and holder therefor, showing the shank of the holder in accordance with the present invention.

Referring now to the drawings, FIG. 1 shows a dental tool 10 according to the present invention. The dental tool 10 includes a dental anchor 12 and a holder 14 therefor, the holder 14 having a shank 16A pursuant to the present invention. The dental anchor 12 is fabricated from metal and includes two threaded sections 18 and 20 joined together by a frangible portion 22 so that the sections can be severed. The holder 14 is provided with an opening for receiving the dental anchor 12 in preferably a force-fit connection therebetween, the holder 14 being preferably fabricated from a plastic material. A similar type of construction as described above is disclosed in my co-pending patent application Ser. No. 887,173, filed Mar. 16, 1978, entitled DENTAL ANCHOR AND A PLASTIC SHANK FOR HOLDING SAME, to which reference may be made for a more detailed description and function thereof, where this construction is shown for illustrative purposes only to indicate a dental tool which can be modified to include the dental tool shank of the present invention. However, it is noted, that the illustrated dental anchor and holder could be formed as a one-piece metal construction and still employ the shank of the present invention.

Figure 2:
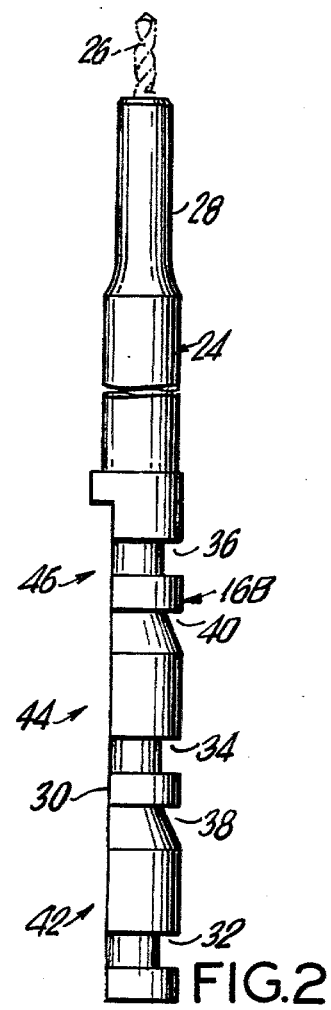
FIG. 2 is an elevational view of a dental tool, such as a dental drill and holder therefor, showing the shank of the holder turned 90° relative to the shank of the holder shown in FIG. 1.

FIG. 2 shows another dental tool 24 in the form of a dental drill having a drill bit 26 connected to the drill bit retaining body 28, both being fabricated from metal materials. The retaining body 28 is provided with a shank 16B pursuant to the present invention. A similar type of construction is disclosed in my U.S. Pat. No. 3,726,014, to which reference may be made for a more detailed description of the structure and function thereof, where this type of dental tool is shown for illustrative purposes only in order to indicate the employment of the shank of the present invention. However, it is again noted that the drill bit and retaining body can be constructed as a one-piece metal structure.

Figure 3:
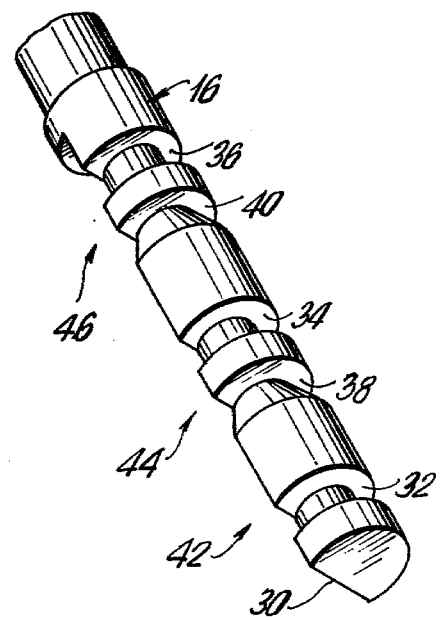
FIG. 3 is a fragmented perspective view of the shank according to the present invention.

Pursuant to the present invention, the shanks 16A and 16B shown on the dental tools of FIGS. 1 and 2 are the same, as best illustrated by the shank 16 shown in FIG. 3. Accordingly, the parts of the shank 16, 16A and 16B will now be discussed below in a more complete description thereof, where the reference numerals of these parts will be the same for each of the shanks for a clearer and better understanding thereof.

Each of the shanks 16, 16A and 16B, and the shanks of other dental tools employing the present invention, are disposed at the head portion of the dental tool and includes a flat or planar surface 30 extending longitudinally along the head portion from the end thereof. The flat surface 30 provides a driving engagement with a shank receiving sleeve provided in the head or tool holder portion of a conventional hand piece to rotate the dental tool in a conventional manner. Longitudinally spaced apart circumferential grooves 32, 34 and 36 are provided on the head portion, being spaced from the end thereof and extending around from opposite sides of the flat surface 30. A selected one of the grooves 32, 34 and 36 receives a conventional latching tongue of the hand piece to prevent the shank from being displaced along its longitudinal axis from the hand piece.

Additionally, the shank head portion is provided with a circumferential tapered notch 38 longitudinally spaced between grooves 32 and 34, and another circumferential tapered notch longitudinally spaced between grooves 34 and 36. The notches 38 and 40 divide the shank head portion into driving and latching arrangement sections 42, 44 and 46 and permits the severance of the sections from each other to limit the extension of the dental tool from the hand piece for convenient access to the operative areas of the patient's mouth without discomfort thereto.

Figure 4:
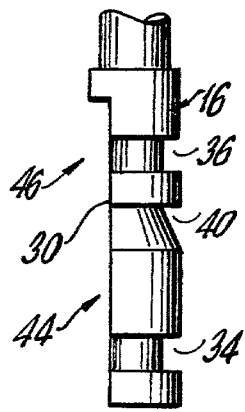
FIG. 4 is a fragmented elevational view showing the shank of FIG. 3 with one section severed therefrom.
Figure 5:
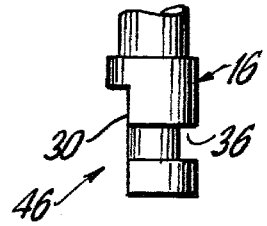
FIG. 5 is a fragmented elevational view similar to FIG. 4 showing the shank having two sections severed therefrom.

FIG. 4 shows the shank 16 with the driving and latching arrangement section 42 severed therefrom, and FIG. 5 shows the shank 16 with both the driving and latching arrangement sections 42 and 44 severed therefrom. The uppermost section or sections may be severed from the shank by the use of a suitable cutting tool, such as snips or pliers well known in the art, in the case of a metal shank, or in the case of a plastic shank a razor blade may be used to sever the desired sections. Though only three sections have been shown, it is of course to be understood that any number of sections may be provided on the shank 16 which may be suitably severed to any desired length. Furthermore, this arrangement may be provided on the shank of a tool of any presently used or conventional hand piece, or may be fabricated from any material that may be developed, where any suitable cutting tool may be employed for achieving the severance along the selected notch which acts as a guide for such cutting.

Figure 6:
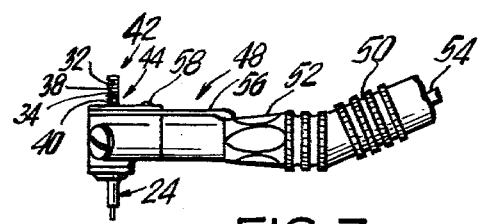
FIGS. 6, 7 and 8 are fragmented elevational views showing the dental drill and holder therefor of FIG. 2 disposed in a conventional dental hand piece, illustrating the variable length of the dental tool shank according to the present invention.
Figure 7:
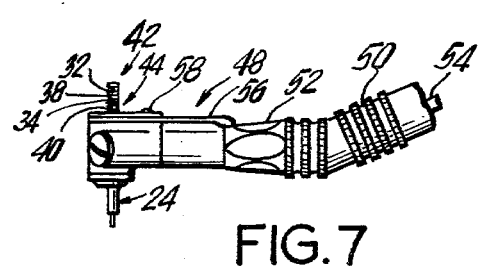
Figure 8:
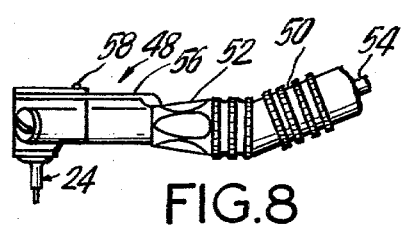

FIGS. 6, 7 and 8 show the dental tool 24 of FIG. 2 disposed in a conventional head or tool holder portion 48 of a conventional dental hand piece to illustrate the variable length of the dental tool shank with respect to the dental hand piece, pursuant to the present invention. The tool holder portion, being of the contra-angle type, includes a coupling member 50 which is provided at one end with a tubular sleeve 52. The coupling member 50 is adapted to receive the chuck end of the hand piece, not shown. The coupling member 50 mounts a drive shaft 54 which is gripped in the chuck of the hand piece so that it can be rotated by the dental engine. The tubular sleeve 52 is provided with a worm gear which is connected to the drive shaft 54 to turn a pinion gear, not shown, which includes a hollow core for receiving the head portion of the dental tool therein so that an internal flat surface of the core engages the flat surface 30 of the shank for rotation thereof.

The tool holder portion 48 is also provided with a latching tongue 56 which is connected thereto by a pivot screw 58 so that a locking slot, not shown, provided in the latching tongue can be pivoted to engage in the selected one of the grooves 32, 34 and 36 of the shank to prevent the shank from displacement along its longitudinal axis from the tool holder portion 48. For a more detailed description of the tool holder portion 48, reference should be made to my U.S. Pat. No. 3,369,298.

As shown in FIG. 6, the dental tool 24 is inserted in a conventional manner into the tool holder portion 48 and is secured therein by the latching tongue 56, where the shank extends its full limit from the tool holder portion. Accordingly, when it is desired to reduce the tool extension to accommodate the limitations of the patient's mouth, the dental tool 24 is extended through the tool holder portion 48 so that the latching tongue is engaged in either groove 34 of the shank, or in groove 36 of the shank as indicated in FIG. 7. Thus, the dentist is able to vary the length of the dental tool which extends outwardly from the tool holder portion 48. Furthermore, when it is desired, the dentist may sever the upper portion or portions from the shank by the use of a suitable cutting tool as set forth above. FIG. 8 illustrates the dental tool 24 secured in the tool holder portion 48, with the upper two sections 42 and 44 severed therefrom, where these portions may be severed prior to insertion into the tool holder portion 48 of the dental hand piece.

Numerous alterations of the structure herein disclosed will suggest themselves to those skilled in the art. However, it is to be understood that the present disclosure relates to a preferred embodiment of the invention which is for purposes of illustration only and is not to be construed as a limitation of the invention.

What is claimed is:

1. A dental tool, such as a drill, burr, anchor and the like, comprising:

a body member provided with an operative end portion for association with teeth of a patient and a shank extending from said operative end portion;

said shank including at least first and second longitudinally extending sections, each of said sections including a first portion having a circumferential groove therein and a second portion having a flat surface, said first portions and said second portions being disposed along longitudinal axis of said shank;

said first portion of said first section being connected to said second portion of said second section with said first portion of said second section being a free end of said shank;

said groove of said first section being longitudinally spaced from said groove of said second section; and said flat surface of said first section being longitudinally spaced from said flat surface of said second section, whereby said shank is receivable in a dental tool holder for operative positioning of the dental tool with respect to the teeth of the patient, and whereby said sections allow selective extension of said shank and said operative end portion with respect to the dental tool holder, and said grooves selectively permit said shank to be removably retainable in the dental tool holder, and said flat surfaces are selectively drivingly engageable with the dental tool holder so that the dental tool holder can rotate said shank.

2. A dental tool according to claim 1, wherein said shank further includes frangible means to facilitate severance of said second section from said first section for shortening longitudinal extension of said shank to permit convenient access to operational areas of the patient's mouth.

3. A dental tool according to claim 2, wherein said frangible means is a circumferential tapered notch disposed in said second portion of said second section.

4. A dental tool according to claim 1, wherein said flat surfaces of said first and second sections define a longitudinally extending planar surface disposed along said first and second sections of said shank.

5. A dental tool according to claim 1, wherein said shank is fabricated from a plastic material.

6. A dental tool according to claim 1, wherein said shank is fabricated from metal.

7. A combination of a dental tool, such as a drill, burr, anchor and the like, and a dental tool holder, such as a dental hand piece and the like, for rotating said dental tool which is receivable in said dental tool holder for operative positioning thereof with respect to teeth of a patient, said combination comprising:

said dental tool including a body member provided with an operative end portion for association with the teeth and a shank extending from the operative end portion for association with said dental tool holder;

said dental tool holder having an aperature receiving said shank therein, said dental tool holder having first means for retaining said shank in said aperture, said dental tool holder being provided with second means for rotating said shank;

said shank including first means for removably engaging said shank in said aperture of said dental tool holder, and second means for providing driving engagement between said shank and said dental tool holder;

said first engaging means including at least two longitudinally spaced apart circumferential grooves in said shank for selectively receiving said first means of said dental tool holder in one of said grooves to vary longitudinal extension of said shank from said dental tool holder; and said second driving means including at least two longitudinally spaced apart flat surface portions on said shank for driving engagement with said second means of said dental tool holder, said two flat surface portions cooperating with said two grooves respectively in each selected extension of said shank.

8. A combination according to claim 7, wherein said shank further includes third means to facilitate severance of one of said flat surface portions and one of said two grooves associated therewith from the other of said flat surface portions and the other of said two grooves associated therewith for shortening said longitudinal extension of said shank to permit convenient access to operative areas of the patient's mouth.

9. A combination according to claim 8, wherein said third means is a circumferential notch longitudinally disposed between said two grooves.

10. A combination according to claim 7, wherein said shank is fabricated from metal.

11. A combination according to claim 7, wherein said shank is fabricated from a plastic material.

12. A combination of a dental tool, such as a drill, burr, anchor and the like, and a dental tool holder, such as a dental hand piece and the like, for rotating said dental tool which is receivable in said dental tool holder for operative positioning thereof with respect to teeth of a patient, said combination comprising:

said dental tool including a body member provided with an operative end portion for association with the teeth and a shank extending from the operative end portion for association with said dental tool holder;

said dental tool holder having an aperture receiving said shank therein, said dental tool holder having first means for retaining said shank in said aperture, said dental tool holder being provided with second means for rotating said shank;

said shank including first means for removably engaging said shank in said aperture of said dental tool holder, and second means for providing driving engagement between said shank and said dental tool holder;

said shank further including third means to facilitate severance of an end section of said shank for shortening longitudinal extension of said shank from said dental tool holder to permit convenient access to operative areas of the patient's mouth; and said shank including at least portions of said first engaging means and said second driving means in each severable section length thereof with remaining portions of said first engaging means and said second driving means being disposed on said shortened extension of said shank.

13. A combination according to claim 12, wherein each said severable section length and said shortened extension of said shank includes a circumferential groove defining said first engaging means and a flat surface defining said second driving means.

14. A combination according to claim 13, wherein said third means is a circumferential notch longitudinally disposed between said grooves of said first engaging means.

15. A combination according to claim 14, wherein said shank includes three of said grooves and one longitudinally extending planar surface defined by said flat surfaces, and two of said notches alternatively disposed between said grooves.

16. A combination according to claim 12, wherein said third means is a circumferential tapered notch.

17. A combination according to claim 12, wherein said shank is fabricated from metal.

18. A combination according to claim 12, wherein said shank is fabricated from a plastic material.

* * * * *